United States Patent [19]

Kaiser et al.

[11] 4,313,856
[45] Feb. 2, 1982

[54] PERFUME COMPOSITIONS CONTAINING OXYGENATED IONONE DERIVATIVES

[75] Inventors: Roman Kaiser, Uster; Dietmar Lamparsky, Wangen-Dübendorf, both of Switzerland

[73] Assignee: Givaudan Corporation, Clifton, N.J.

[21] Appl. No.: 194,651

[22] Filed: Oct. 6, 1980

Related U.S. Application Data

[60] Continuation of Ser. No. 68,921, Aug. 23, 1979, abandoned, which is a division of Ser. No. 889,070, Mar. 22, 1978.

[30] Foreign Application Priority Data

Mar. 28, 1977 [AT] Austria .................... 2158/77

[51] Int. Cl.³ .................... C11B 9/00
[52] U.S. Cl. .................... 252/522 R; 568/377
[58] Field of Search .................... 252/522 R

[56] References Cited

U.S. PATENT DOCUMENTS

| | | | |
|---|---|---|---|
| 3,217,718 | 11/1965 | Roberts | 131/17 R |
| 3,268,589 | 8/1966 | Rowland | 260/586 R |
| 3,962,148 | 6/1976 | Hochstetler | 252/522 R |
| 4,246,292 | 1/1981 | Konst et al. | 252/522 R |

OTHER PUBLICATIONS

Demole et al., Helv. Chim. Acta. 55, 1866 (1972).
Aasen et al., Acta. Chim. Scand. 26, No. 6, 2573 (1972).
Stork et al., J. Am. Chem. Soc. 93 (22), 5938–5939 (1971).
Ohloff Lecture delivered, 10/7/77–10/11/77.
Lloyd et al., Tobacco Internt'l 78, No. 7, 125-133 (1976).

*Primary Examiner*—John F. Niebling
*Attorney, Agent, or Firm*—Robert F. Tavares; Thomas Cifelli, Jr.

[57] ABSTRACT

The preparation and use as odorant and/or flavorant of compounds having the formula:

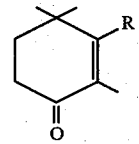

I wherein R represents a butyl, but-2-en-yl or 1,3-butadienyl group.

9 Claims, No Drawings

PERFUME COMPOSITIONS CONTAINING OXYGENATED IONONE DERIVATIVES

This is a continuation of application Ser. No. 068,921 filed Aug. 23, 1979, abandoned, which is a division of Ser. No. 889,070, filed on Mar. 22, 1978.

FIELD OF THE INVENTION

This invention relates to the field or odorants and flavorants.

SUMMARY OF THE INVENTION

The present invention relates to novel odorant and-/or flavoring substances. More particularly, the invention is concerned with compounds of the general formula

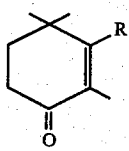
(I)

wherein

R represents a butyl, but-2-en-yl or 1,3-butadienyl group, a process for the manufacture thereof and odorant and/or a flavoring compositions containing same. The invention is also concerned with a method of imparting an odor and/or flavor to materials using said compounds of formula I or said compositions.

DESCRIPTION OF PREFERRED EMBODIMENTS

Formula I hereinbefore is intended to collectively embrace compounds of the formula

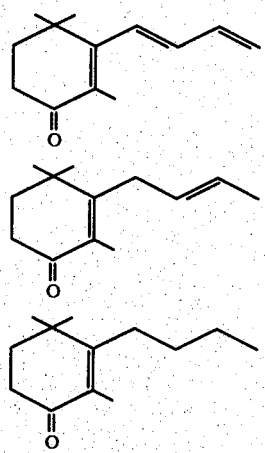

Ia

Ib

Ic

The foregoing formula are intended to embrace all possible geometric isomers having regard to the cis/trans isomerism present.

According to the process provided by the present invention, the compounds of formula I hereinbefore are manufactured by (a) heating 4-(2,6,6-trimethyl-3-oxo-1-cyclohexen-1-yl)-but-3-en-2-ol in an acid medium and, if desired, hydrogenating the exocyclic double bonds present in the reaction product obtained, or (b) subjecting 3-oxodihydro-$\beta$-ionyl acetate to pyrolysis.

The acid medium required for embodiment (a) of the process aforesaid can be produced with the aid of mineral acids such as sulphuric acid or hydrochloric acid, acid salts such as bisulphates (e.g. potassium bisulphate) or acidic earths such as diatomaceous earth (e.g. Filtrol). However, suitable organic acids such as those organic acids which are moderately strong to strong can also be used. Examples of such organic acids are aryl and alkanesulphonic acids (e.g. p-toluenesulphonic acid, methanesulphonic acid) and picric acid.

The reaction temperature is not critical. It conveniently lies in the range of ca 20°–200° C., preferably 60°–130° C. The temperature is conveniently higher when a weaker acid is used and lower when a stronger acid is used.

The reaction is preferably carried out in the presence of an organic solvent, especially an aromatic solvent such as benzene, toluene, xylene etc.

The hydrogenation of the exocyclic double bonds present in a compound of formula Ia is carried out according to methods known per se, conveniently catalytically. Suitable catalysts are noble metals (e.g. palladium, platinum and rhenium) or nickel (e.g. Raney-nickel) etc. The hydrogenation is preferably carried out in the presence of a solvent such as water, ethanol, methanol, dioxan etc.

The hydrogenation is conveniently carried out at room temperature, although it can also be carried out at a lower or higher temperature (e.g. 5° C. to 100° C.) depending on the catalyst and solvent used.

The pyrolysis of the known 3-oxo-dihydro-$\beta$-ionyl acetate [see, for example, H. Ide, S. Toki, Biochem. J. 119, 281 (1970)] in order to manufacture the compound of formula Ib in accordance with embodiment (b) of the process aforesaid is conveniently carried out at a temperature of 350°–700° C., especially at 400°–500° C.

The pyrolysis is conveniently carried out in an inert gas atmosphere (e.g. under nitrogen).

In the manufacture of compounds of formulae Ia and Ib there are usually obtained mixtures of cis/trans isomers. In the case of compounds of formula Ia the trans isomer predominates to an extent of ca 93% and in the case of compounds of formula Ib the trans/cis ratio is ca 4:1. The separation of a cis/trans mixture into the individual isomers is not necessary, but is possible. Thus, for example, the separation can be carried out according to known techniques such as column chromatography, preparative gas chromatography etc.

The compounds of formula I have particular organoleptic properties, on the basis of which they are excellently suited as odorant and/or flavouring substances.

The invention is therefore also concerned with a method of imparting an odour and/or a flavour to materials, which method comprises applying to said materials or incorporating therein an odour- and/or a flavour-imparting amount of a compound of formula I in practically pure form or in the form of mixtures (with the exception of natural mixtures containing a compound of formula I) or of an odorant and/or flavouring composition containing same.

The expression "practically pure" is used herein to mean, in particular, a compound of formula I which is free from accompanying substances which are present besides compounds of formula I in natural extracts. As practically pure compounds of formula I in the scope of the present invention there should be understood, in particular, synthetically manufactured compounds of formula I.

The compounds of formula I, and especially those of formula Ia, have fine, tea-like, spicy, slightly woody olfactory nuances reminiscent of dried fruits. They can therefore be used, for example, for the perfuming or flavoring of products such as cosmetics (soaps, saves, powders etc), detergents or foodstuffs, luxury consumables and drinks, the compounds preferably not being used alone but rather in the form of compositions which contain other odorant or flavouring substances. Such odorant or flavouring substance compositions containing a compound of formula I and their production in a manner known per se (the addition of a compound of formula I to known odorant or flavouring substance compositions or the admixture of a compound of formula I with natural or synthetic compounds or mixtures suitable as components of odorant or flavouring substance compositions) likewise form part of the present invention.

On the basis of their very natural notes, the compounds of formula I, and especially those of formula Ia, are suitable as odorants, especially in combination with a series of natural and synthetic odorant substances such as, for example, galbanum, mastix, vetiver oil, patchouli oil, bergamot oil, petitgrain oil, basil oil, tree moss absolute, jasmine absolute, aldehydes, acetals, ketones, alcohols, esters, lactones, ethers, sulphur-containing compounds (e.g. p-menthane-8-thiol-3-one etc), heterocyclic compounds, e.g. nitrogen-containing compounds (e.g. indole etc), 5-methyl-heptan-3-onoxime, aliphatics, e.g. methyl anthaninlate, and musk compounds. They also perform in a very good manner in creating synthetic perfume oils, i.e. of the roseoil type to which they impart interesting tea rose notes as well as strong diffusion and radiation power.

The odorant compositions containing the compounds of formula I are especially attractive by their impressive freshness. In this connection, the compounds of formula I hereinbefore differ in a fundamental manner from the known megastigmatrienones of similar structure [Acta. Chem. Scand. 26, 2573 (1972), U.S. Pat. No. 3,268,589, U.S. Pat. No. 3,217,718]. These known trienones of the formulae

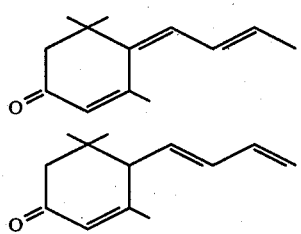

U.S. Pat. No. 3 268 589

U.S. Pat. No. 3 217 718 yield compositions having heavy, sweet olfactory impressions.

The concentration of the compounds of formula I can vary within wide limits depending on the purpose of use; for example, between about 0.01 wt.% in the case of detergents and about 15 wt.% in the case of alcoholic solutions. In perfume bases or concentrates, the concentration can, of course, also be higher. The perfume bases can be used in the customary manner for the perfuming of Eau de Cologne, eau de toilette, lotions, creams, shampoos, soaps, detergents etc.

As flavouring substances, the compounds of formula I can be used, for example, for the production or improvement, intensification, enhancement of modification of fruit or berry aromas in foodstuffs (yoghurt, sweet goods (candies, jellies etc), in luxury consumables (tea etc) and drinks, e.g. soft drinks (lemonades etc), in tobacco flavouring.

The pronounced flavour qualities of especially practically pure, and particularly of synthetically manufactured, compounds of formula I enable them to be used in low concentrations. A suitable range is, for example, 0.1 ppm–100 ppm, preferably 1 ppm–20 ppm, in the finished product (i.e. the aromatised foodstuff, luxury consumable or drink). In tobacco flavouring, the concentration can be higher.

The following Table illustrates some effects which can be achieved with the compounds of formula I.

TABLE

| Aroma | Amount | Effect |
| --- | --- | --- |
| Raspberry | ppm in the finished product 0.1–30 ppm especially 0.5–4 ppm | greater naturality, fruit character, full aroma |
| Tea | ppm in the finished product 0.1–100 ppm especially 1 –20 ppm | very natural tea character |

The compounds of formula I can be mixed with the ingredients used for flavouring substance compositions or added to such flavourants in the usual manner. Among the flavourants contemplated in accordance with the present invention there are to be understood flavouring compositions which can be diluted or dispersed in edible materials in a manner known per se. They can be converted according to methods known per se into the usual forms of use such as solutions, pastes or powders. The products can be spray-dried, vacuum-dried or lyophilised.

For the production of such usual forms of use there come into consideration, for example, the following carrier materials, thickening agents, flavour-improvers, spices, auxilary ingredients etc:

Gum arabic, tragacanth, salts or brewers' yeast, alginates, carrageens or similar absorbents; indoles, maltol, spice oleoresins, smoke aromas; cloves, sodium citrate; monosodium glutamate, disodium inosine-5'-monophosphate (IMP), disodium guanosine-5-phosphate (GMP); or special flavour substances, water, ethanol, propyleneglycol, glycerine.

The following Examples illustrate the process provided by the present invention:

EXAMPLE 1

A solution of 70 g of crude 3-oxo-β-ionol and 1.5 g of paratoluenesulphonic acid in 300 ml of toluene is stirred at reflux temperature for 40 minutes with simultaneous removal of the water formed by means of a water separator. The cooled mixture is treated with 300 ml of ether, the organic phase is washed three times with soda solution and three times with water, dried and concentrated. There are obtained 61 g of crude product which contains more than 90% of 2,4,4-trimethyl-3-(buta-1,3-dienyl)cyclohex-2-en-1-one according to gas-chromatographical analysis. Distillation of the crude product over a 15 cm column gives 45 g of olfactorily-good 2,4,4-trimethyl-3-(buta-1,3-dienyl)cyclohex-2-en-1-one of boiling point 74°–75° C./0.06 mm Hg.

IR: 1665, 1595, 1350, 1299, 1199, 1090, 1005, 902 cm$^{-1}$;

NMR: 1.20 (6H, 2s); 1.86 (3H, s); 1.84 (2H, m); 2.48 (2H, m); 5.1–5.5 (2H, m); 6.1–6.8 (3H, m) (δ in ppm);

MS: 190 (72), 175 (42), 134 (73), 133 (67), 119 (81), 105 (58), 91 (100), 77 (44), 55 (47), 41 (85), 39 (56);

UV: λmax$_1$ 223 nm (ε$_1$=12800, ethanol); λmax$_2$ 294 nm (ε$_2$=12770).

The 3-oxo-β-ionol used as the starting material can be prepared as follows:

To a suspension, cooled to 10° C. and well-stirred, of 192 g (1 mol) of α-ionone and 198 g of anhydrous sodium acetate in 1 liter of methylene chloride are added dropwise over a period of 1 hour 200 g (ca 1.05 mol) of 40% peracetic acid in such a manner than the temperature does not exceed 20° C. The external cooling source is then removed and the mixture is stirred at room temperature for 5 hours. In the course of the first hour the temperature of the mixture rises to 28° C. and thereafter again falls slowly. The mixture is freed from sodium acetate by filtration and the clear solution is washed twice with water, four times with soda solution and once again with water until it is neutral. After drying over sodium sulphate and concentration, there are obtained 215 g of crude product which contains more than 94% of α-ionone epoxide according to gas-chromatographical analysis.

To a solution of 215 g (ca 1 mol) of crude α-ionone epoxide in 700 ml of methanol is added dropwise over a period of 5 minutes a freshly prepared sodium methylate solution (obtained by dissolving 2.9 g of sodium in 100 ml of methanol). The mixture is then stirred at the reflux temperature of the methanol for 3 hours, half of the methanol is distilled off under a water-jet vacuum, the concentrate is treated with a four-fold amount of water and the product is extracted with ether. After drying and concentration of the ether phase, there are obtained 213 g of crude product which contains more than 85% of 4-(2,6,6-trimethyl-3-hydroxy-cyclohex-1-en-1-yl)-but-3-en-2-one according to gas-chromatographical analysis. Distillation of the crude product over a 15 cm Widmer column gives 155 g (75% yield based on α-ionone used) of product having a purity above 94% and a boiling point of 131°–132° C./0.05 mm Hg.

IR: 3420, 1670, 1609, 1254, 1175, 1077, 1025, 998, 979, 962 cm$^{-1}$;

NMR: 1.08 and 1.09 (each 3H, s); 1.86 (3H, s); 2.33 (3H, s); 4.04 (1H, m); 6.10 (1H, d, J~16 cps); 7.24 (1H, d, J~16 cps) δ ppm;

MS: m/e 208 (33), 137 (15), 123 (22), 109 (67), 93 (12), 91 (15), 55 (12), 43 (100), 41 (26), 39 (15).

To a solution, pre-cooled to 0° C., of 140 g (0.068 mol) of 4-(2,6,6-trimethyl-3-hydroxy-cyclohex-1-en-1-yl)-but-3-en-2-one in 500 ml of ether are added dropwise over a period of 10 minutes 700 ml of an aqueous solution, cooled to 0° C., of 202.6 g of sodium dichromate dihydrate and 186 g of concentrated sulphuric acid with intensive cooling and good stirring so that a temperature of 5° C. is not exceeded. The mixture is then stirred for a further 5 minutes at 5° C., treated with 500 ml of ether, the ether phase is washed three times with water, three times with soda solution and again three times with water, dried over sodium sulphate and concentrated. Distillation of the resulting 125 g of crude product over a 10 cm Widmer column gave 103 g of more than 94% g of more than 94% pure 4-(2,6,6-trimethyl-3-oxo-cyclohex-1-en-1-yl)-but-3-en-2-one of boiling point 109°–110° C./0.05 mm Hg; melting point 50°–51° C.

IR: 1665, 1615, 1248, 1173, 978 cm$^{-1}$ (in chloroform);

NMR: 1.19 (6H, 2s); 1.79 (3H, s); 1.85 (2H, t, J~7 cps); 2.33 (3H, s); 2.52 (2H, t J~7 cps); 6.12 (1H, d, J~16 cps); 7.21 (1H, d, J~16 cps) δ ppm;

MS: m/e 206 (7), 163 (21), 135 (10), 121 (19), 91 (15), 77 (12), 65 (12), 55 (16), 43 (100), 41 (28), 39 (20).

To a solution, cooled to 10° C., of 72 g (0.35 mol) of 4-(2,6,6-trimethyl-3-oxo-cyclohex-1-en-1-yl)-but-3-en-2-one in 400 ml of methanol are added portionwise over a period of 10 minutes with simultaneous stirring and external cooling a total of 4.0 g (0.106 mol) of sodium borohydride in such a manner that the temperature does not exceed 13° C. The mixture is then stirred for a further 15 minutes at 10° C., treated with a four-fold amount of water and the product is extracted with ether. After drying and concentration of the ether solution, there are obtained 73 g of crude product which contains more than 90% of 4-(2,6,6-trimethyl-3-oxo-cyclohex-1-en-1-yl)-but-3-en-2-ol (3-oxo-β-ionol). 3 g of the crude product are purified by column chromatography. The product, which is more than 97% pure, is used for the characterisation.

IR: 3420, 1660, 1595, 1200, 1139, 1095, 1030, 970, 940 cm$^{-1}$;

NMR: 1.18 (6H, 2s); 1.37 (3H, d, J~7 cps); 1.89 (2H, t, J~7 cps); 2.52 (2H, t, J~7 cps); 4.50 (1H, m), 5.70 (1H, d from d, J$_{AB}$~16 cps, J$_{AX}$~5.5 cps); 6.27 (1H, d, J~16 cps);

MS: m/e 208 (8), 193 (22), 165 (100), 137 (26), 109 (22), 107 (24), 91 (22), 77 (20), 55 (21), 43 (69), 41 (43).

EXAMPLE 2

The pyrolysis apparatus consists of a quartz tube having a length of 50 cm and a diameter of 5 cm, which is filled with glass rings of 2–4 mm diameter and is conditioned to a temperature of 500° C. with a heating mantle.

8.0 g (0.034 mol) of 3-oxodihydro-β-ionyl acetate are dissolved in 30 ml of benzene and dropped into the pyrolysis tube over a period of 20 minutes while simultaneously passing through a nitrogen stream of 0.3 liter/minute. The pyrolysis product is condensed in a cooled vessel, diluted with 30 ml of hexane, washed twice with a sodium bicarbonate solution and twice with water, dried and concentrated. Distillation of the resulting crude product (5.0 g) over a 5 cm Widmer column gives 3.5 g of product of boiling point 69°–70° C./0.05 mm Hg, which is composed of 80% of 2,4,4-trimethyl-3-(but-trans-2-en-1-yl)-cyclohex-2-en-1-one and of 20% of the corresponding cis isomer. A sample purified by preparative gas chromatography is used for the characterisation:

IR: 1670, 1610, 1199, 1082, 1030, 965 cm$^{-1}$;

NMR: 1.13 (6H, 2s); 1.75 (3H, s); 1.69–1.75 (3H); 1.82 (2H, m); 2.48 (2H, m); 2.98 (2H); 5.4 (2H, m) δ ppm;

MS: 192 (57), 138 (39), 137 (100), 121 (37), 109 (47), 93 (27), 81 (29), 77 (26), 67 (25), 55 (40), 41 (72).

The compound has a balsamic, camphoraceous, fruity, woody odour and is reminiscent in certain respects of myrrh and opopanax.

EXAMPLE 3

A solution of 3.80 g (0.02 mol) of 2,4,4-trimethyl-3-(buta-1,3-dienyl)-cyclohex-2-en-1-one, prepared as described in Example 1, in 20 ml of ethanol is treated with 0.1 g of catalyst (palladium, 10% on charcoal) and the mixture is hydrogenated at normal pressure until 0.04 mol of hydrogen has been taken up. After filtration, concentration and bulb-tube distillation, there are obtained 3.2 g of product which contains more than 85% of 2,4,4-trimethyl-3-butyl-cyclohex-2-en-1-one according to gas-chromatographical analysis.

IR: 1670, 1610, 1199, 1080, 1032 cm$^{-1}$;

NMR: 0.93 (3H, t, J~6 cps); 1.14 (6H, 2s), 1.76 (3H, s); 1.80 (2H, m); 2.48 (2H, m) δ ppm;

MS: 194 (21), 138 (40), 137 (100), 123 (17), 109 (50), 95 (25), 81 (23), 67 (21), 55 (43), 41 (60).

The compound has a cedarlike-woody, green, slightly spicy, fruity odour.

EXAMPLE 4

2,4,4-Trimethyl-3-(but-trans-2-en-1-yl)-cyclohex-2-en-1-one, prepared as described in Example 2, can also be catalytically hydrogenated in a manner analogous to that described in Example 3 to give 2,4,4-trimethyl-3-butyl-cyclohex-2-en-1-one. The yield is 82%.

The following Examples A to M demonstrate how a wide palette of odorant bases can be enriched or improved in a desirable manner by addition of compounds of formula I, or also how bases of quite novel odour directions can be produced. In the compositions of Examples A–K, the effect realised by compounds of formula I could not be obtained by addition of the same amounts of megastigmatrienones (in the form of their mixtures). All such compositions lacked, in particular, the characteristic freshness which is conveyed to them by the addition of compounds of formula I. Particularly noticeable, moreover, is the fact that compounds of formula I in combination with certain known perfumery raw materials (see Examples D, H) lead to a tobacco note not previously observable, which surprisingly can not be realised by addition of the megastigmatrienones which are known as tobacco components.

EXAMPLE A

| Green base | Parts by weight |
| --- | --- |
| α-Hexylcinnamaldehyde | 200 |
| Phenylethyl formate | 200 |
| n-Hexylsalicylate | 200 |
| Galbanum synthetic | 60 |
| Propylphenylethyl acetal | 60 |
| Isocyclocitral | 50 |
| Cyclal (Trade Mark) (2,4-dimethyl-cyclohexen-1-carboxaldehyde | 20 |
| Acetanisole | 20 |
| p-Menthane-8-thiol-3-one | 10 |
| Mastix oil absolute | 10 |
| Stemone (Trade Mark) (3-methyl-5-heptanoxime) | 10 |
| | 840 |

By addition to this green base of 160 parts by weight of the compound of formula Ia, the somewhat hard green of the base is rounded off very well. If the galbanum odour-fixation mainly acts in the green base, then with the addition of the compound of formula Ia the soft green of the mastix absolute is desirably underlined. The base now acts much more flowery.

EXAMPLE B

| Petitgrain composition | Parts by weight |
| --- | --- |
| Phenylethyl alcohol | 240 |

-continued

| Petitgrain composition | Parts by weight |
| --- | --- |
| Linalyl acetate | 200 |
| Linalool extra | 160 |
| Terpineol | 100 |
| Nerol extra | 100 |
| Methyl antranilate | 60 |
| Methyl napthyl ketone | 40 |
| Geranyl acetate | 40 |
| | 940 |

By addition of 60 parts of the compound of formula Ia this petitgrain composition is altered very strongly in the direction of Cologne. It is much fresher and now possesses a delicate rose note in the direction of tea-rose.

| Flowery composition (rose direction) | Parts by weight |
| --- | --- |
| Phenylethyl-phenyl acetate | 400 |
| Geraniol extra | 300 |
| Nerol extra | 100 |
| Rhodinol pure | 60 |
| Citronellyl acetate | 20 |
| Cinnamyl alcohol | 20 |
| | 900 |

After addition of 100 parts by weight of the compound of formula Ia, this flowery base acts clearly less sweet, fresher, rounder, herbaceous and slightly spicy.

EXAMPLE D

| Perfumery complex (wood direction) | Parts by weight |
| --- | --- |
| Sandalwood oil | 340 |
| Patchouli oil | 340 |
| Vetiver oil | 200 |
| Cedryl acetate | 60 |
| | 940 |

Addition to this woody complex of 60 parts of the compound of formula Ia unexpectedly underlines the vetiver-patchouli direction therein. The complex simultaneously takes on a very valuable tobacco note for men's lines, which can not be achieved in this manner with the known megastigmatrienones.

EXAMPLE E

| Perfumery complex | Parts by weight |
| --- | --- |
| Methyl dihydrojasmonate | 600 |
| Bergamot oil | 300 |
| Patchouli oil | 40 |
| | 940 |

By addition of 60 parts of the compound of formula Ia the bergamot note in this complex is strongly displayed and the fresh effect especially emphasised.

EXAMPLE F

| Flowery perfumery composition | Parts by weight |
| --- | --- |
| Phenylethyl-phenyl acetate | 250 |
| Phenylethyl alcohol | 200 |
| Nopyl acetate | 200 |
| Phenylacetaldehyde-glyceryl acetal | 100 |
| Methyl dihydrojasmonate | 100 |
| Hydroxycitronellal | 60 |

| Flowery perfumery composition -continued | Parts by weight |
|---|---|
| Cyclamen aldehyde | 40 |
| Syringa aldehyde | 10 |
| Benzyl acetate | 10 |
| Linalool extra | 10 |
| Indole (10% in ethyl phthalate) | 6 |
| $C_{11}$-aldehyde (10% in ethyl phthalate) | 4 |
| | 990 |

When there are added to this flowery composition 10 parts of the compound of formula Ia, the composition is desirably rounded, and it now acts softer and desirably in the direction of muguet.

EXAMPLE G

| Perfumery composition (tea direction) | Parts by weight |
|---|---|
| Bergamot oil | 200 |
| α-Hexylcinnamaldehyde | 160 |
| Geraniol extra | 120 |
| Linalool extra | 120 |
| Allylphenoxy acetate | 120 |
| Methylisoeugenol | 120 |
| Petitgrain oil Paraguay | 60 |
| Basil oil | 60 |
| | 960 |

When there are added to this basic composition (Cologne direction) 40 parts of the compound of formula Ia, the composition is brought very well in the direction of tea. There sets in a very fresh, slightly tert.but. rather herbaceous effect which underlines the peel note of the citrus ingredients in this composition.

EXAMPLE H

| Chypre composition | Parts by weight |
|---|---|
| Bergamot oil | 300 |
| Citronellol extra | 200 |
| Patchouli oil | 100 |
| Vetiver oil | 100 |
| Hydroxycitronellal | 100 |
| Eugenol extra | 80 |
| Tree moss absolute (50% in ethyl phthalate) | 20 |
| Styrallyl acetate | 20 |
| Methylnonyl acetaldehyde (10% in ethyl phthalate) | 20 |
| | 940 |

When there are added to this Chypre composition 60 parts of the compound of formula Ia, the composition is considerably less woody, it is fresher, more herbaceous and there is obtained a very fine tobacco note.

EXAMPLE I

| Cologne base | Parts by weight |
|---|---|
| Bergamotte oil | 200 |
| Geraniol extra | 200 |
| Hydroxycitronellal | 200 |
| Methyl 1-methylcyclododecyl ether | 200 |
| N-Hexyl salicylate | 100 |
| Galbanum oil | 10 |
| Cyclamen aldehyde | 10 |
| | 920 |

When there are added to this Cologne base 80 parts of the compound of formula Ib, the resulting base acts much fresher, dry-herbaceous and gives the impression of cleanliness in consumers' products. In the novel base the citrus peel character is brought into prominence in a desirable manner.

EXAMPLE J

| Lily of the valley base | Parts by weight |
|---|---|
| Alcohol 96° | 110 |
| Phenylethyl alcohol | 300 |
| Hydroxycitronellal | 300 |
| Benzyl acetate | 150 |
| Methyl dihydrojasmonate | 30 |
| Linalool extra | 20 |
| Citronellol | 20 |
| Citronellyl acetate | 10 |
| Cyclamen aldehyde | 10 |
| | 950 |

When there are added to this conventional lily of the valley base 50 parts of the compound of formula Ib, the novel base acts much rounder, softer and more flowery. The somewhat hard note of the benzyl acetate is suppressed. The novel base surprisingly takes on an impressive ylang note.

EXAMPLE K

| Perfume composition with rose character | Parts by weight |
|---|---|
| Phenylethyl alcohol | 300 |
| Geraniol extra | 250 |
| Jasmin "lavage" | 200 |
| Citronellol extra | 100 |
| Musk ketone | 50 |
| α-Ionone | 30 |
| $C_{10}$-aldehyde (10% in propyleneglycol) | 5 |
| $C_{11}$-aldehyde (10% in propyleneglycol) | 5 |
| | 940 |

When there are added to this conventional rose composition 60 parts of the compound of formula Ic, the odour characteristic is altered towards the valuable direction of tea rose. If the citronellol dominates in the original base, then in the novel base the geraniol is in the foreground. The novel base acts much more flowery. It has more radiation power and diffusion.

EXAMPLE L

| Raspberry aroma | Parts by weight A | B |
|---|---|---|
| Acetic acid | 1.0 | 1.0 |
| Acetic acid isoamyl ester (10% in propyleneglycol) | 1.5 | 1.5 |
| Dimethylsulphide (10% in propyleneglycol) | 2.0 | 2.0 |
| Vanillin | 2.0 | 2.0 |
| Acetic acid benzyl ester | 3.0 | 3.0 |
| Lemarome (Trade Mark) (citral) (1% in propyleneglycol) | 4.0 | 4.0 |
| Raspberry aroma | 20.0 | 20.0 |
| Propyleneglycol | 966.5 | 957.5 |
| Compound of formula Ia (1% in propyleneglycol) | — | 9.0 |
| | 1000.0 | 1000.0 |

Dosage 100 g/100 liters

By addition of the compound of formula Ia there is attained in aroma B the impression of a much greater naturalness in that the substantially woody note which is now developed advantageous underlines the fruit character and thus confers to the conventional raspberry aroma A more fullness and fruitiness.

EXAMPLE M

| Tea aroma | Parts by weight | |
|---|---|---|
| | A | B |
| Linalool synthetic (1% in propyleneglycol) | 1.0 | 1.0 |
| Camphor (1% in propyleneglycol) | 1.5 | 1.5 |
| Acetic acid linalyl ester (1% in propyleneglycol) | 2.0 | 2.0 |
| Vanillin | 2.0 | 2.0 |
| Lemarome (citral) (1% in propyleneglycol) | 3.0 | 3.0 |
| Tannin (tannic acid) (5% in H₂O) | 100.0 | 100.0 |
| Propyleneglycol | 890.5 | 887.5 |
| Compound of formula Ia (1% in propyleneglycol) | — | 3.0 |
| | 1000.0 | 1000.0 |
| Dosage 400 g/100 liters (10% sugar syrup) | | |

When the compound of formula Ia is added to the conventional, but less typical, flavour A, there is obtained a tea aroma B which, upon tasting in a 10% sugar syrup solution, immediately establishes the impression of genuine black tea.

What is claimed is:

1. A perfume composition comprising an effective amount of a compound having the formula

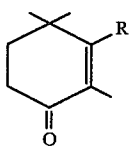

wherein R represents a butyl, but-2-en-1-yl or 1,3-butadienyl, and at least one other olfactory substance excepting those compositions wherein compound I is present as part of a mixture which was derived from, or is identical to a mixture derived from, natural sources.

2. A perfume composition in accordance with claim 1, wherein said compound is 2,4,4-trimethyl-3-(buta-1,3-dienyl)-cyclohex-2-en-1-one (Ia).

3. A perfume composition in accordance with claim 1, wherein said other olfactory substance is selected from the group consisting of galbanum, mastix, vetiver oil, patchouli oil, bergamotte oil, petitgrain oil, basil oil, tree moss absolute, jasmine absolute, aldehydes, acetals, alcohols, ketones, esters, lactones, ethers, p-menthane-8-thiol-3-one, indole, 5-methyl-heptan-3-onoxime, methylanthranilate, and musk compounds.

4. A composition according to claim 1 wherein R is a but-2-en-1-yl group.

5. A composition according to claim 1 where R is a butyl group.

6. A method for improving a perfume composition which comprises adding thereto an effective amount of a compound of the general formula

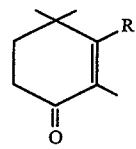

wherein R represents butyl, but-2-en-1-yl or a 1,3-butadienyl group with the exception that I is not added as part of a naturally occurring mixture.

7. The method according to claim 6 wherein the compound added is 2,4,4-trimethyl-3-(buta-1,3-dienyl)-cyclohex-2-en-1-one.

8. The method according to claim 6 wherein the compound added is 2,4,4-trimethyl-3-(but-2-en-1-yl)-cyclohex-2-en-1-one.

9. The method according to claim 6 wherein the compound added is 2,4,4-trimethyl-3-butylcyclohex-2-en-1-one.

* * * * *